United States Patent [19]

Summers

[11] Patent Number: 4,822,811

[45] Date of Patent: Apr. 18, 1989

[54] CARBAZOLE LIPOXYGENASE INHIBITING COMPOUNDS, COMPOSITIONS AND USE

[75] Inventor: James B. Summers, Libertyville, Ill.

[73] Assignee: Abbott Laboratories, Abbott Park, Ill.

[21] Appl. No.: 208,350

[22] Filed: Jun. 17, 1988

Related U.S. Application Data

[63] Continuation-in-part of Ser. No. 120,301, Nov. 13, 1987, Pat. No. 4,769,387.

[51] Int. Cl.$^4$ .................. A61K 31/40; C07D 209/86; C07D 209/88
[52] U.S. Cl. .............................. 514/411; 514/314; 514/339; 546/171; 546/173; 546/175; 546/272; 548/441; 548/444
[58] Field of Search .............. 546/171, 173, 175, 272; 548/441, 444; 514/314, 339, 411

[56] References Cited

U.S. PATENT DOCUMENTS 3,655,697  4/1972  Shen et al. .................. 548/441
3,896,145  7/1975  Berger et al. ................ 548/444

Primary Examiner—Robert W. Ramsuer
Attorney, Agent, or Firm—Steven F. Weinstock; Martin L. Katz

[57] ABSTRACT

Compounds of the formula:

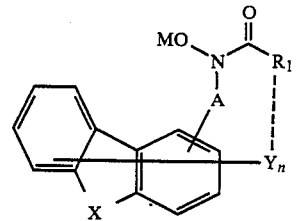

wherein
R1 is hydrogen, C1 to C4 alkyl, C2 to C4 alkenyl, or NR2R3, wherein R2 and R3 are independently selected from hydrogen, C1 to C4 alkyl and hydroxyl, but R2 and R3 are not simultaneously hydroxyl;
X is oxygen, sulfur, CO2, or NR4, wherein R4 is hydrogen, C1 to C6 alkyl, C1 to C6 alkoyl or aroyl;
A is selected from C1 to C6 alkylene and C2 to C6 alkenylene;
Y is selected independently at each occurrence from hydrogen, halogen, hydroxy, cyano, nitro, halo-substituted alkyl, C1 to C12 alkyl, C2 to C12 alkenyl, C1 to C12 alkoxy, C3 to C8 cycloalkyl, aryl, aryloxy, aroyl, C1 to C12 arylalkyl, C2 to C12 arylalkenyl, C1 to C12 arylalkoxy, C1 to C12 arylthicalkoxy, and substituted derivatives of aryl, aryloxy, aroyl, C1 to C12 arylalkyl, C2 to C12 arylalkenyl, C1 to C12 arylalkoxy, or C1 to C12 arylthioalkoxy, wherein C12 alkyl, alkoxy, and halo-substituted alkyl; n is a number having the values 0-4; when n=0 then Y=hydrogen;
and M is hydrogen, a pharmaceutically acceptable cation, aroyl, or C1 to C12 alkoyl. These compounds are potent inhibitors of 5- and/or 12-lipoxygenase enzymes. Also disclosed are lipoxygenase inhibiting compositions and a method of inhibiting lipoxygenase.

10 Claims, No Drawings

CARBAZOLE LIPOXYGENASE INHIBITING COMPOUNDS, COMPOSITIONS AND USE

CROSS-REFERENCE TO RELATED APPLICATIONS

This is a continuation-in-part of Ser. No. 120,301, filed Nov. 13, 1987 now U.S. Pat. No. 4,769,387.

Technical Field

This invention relates to organic compounds which inhibit lipoxygenase enzymes. It also relates to methods and compositions for inhibiting lipoxygenase enzymes in human and animal hosts in need of such treatment.

2. BACKGROUND OF THE INVENTION

The lipoxygenases are a family of enzymes which catalyze the oxygenation of arachidonic acid. The enzyme 5- lipoxygenase converts arachidonic acid to 5-hydroperoxyeicosatetraenoic acid (5-HPETE). This is the first step in the metabolic pathway yielding 5-hydroxyeicosatetraenoic acid (5-HETE) and the important class of mediators of inflammation, the leukotrienes (LTs).

Similarly, 12- and 15-lipoxygenase convert arachidonic acid to 12- and 15-HPETE, respectively. Biochemical reduction of 12-HPETE leads to 12-HETE, while 15-HPETE is the precursor of the class of biological agents known as the lipoxins.

A variety of biological effects are associated with these products from lipoxygenase metabolism of arachidonic acid and they have been implicated as mediators in various disease states. For example, the LTs C4 and D4 are potent constrictors of human airways in vitro, and aerosol administration of these substances to non-asthmatic volunteers induces broncho-constriction. LTB4 and 5-HETE are potent chemotactic factors for inflammatory cells such as polymorphonuclear leukocytes. They also have been found in the synovial fluid of rheumatoid arthritic patients. Leukotrienes have also been implicated as important mediators in allergic rhinitis, psoriasis, adult respiratory distress syndrome, Crohn's disease, endotoxin shock, and ischemia induced myocardial injury among others. The biological activity of the LTs has been reviewed by Lewis and Austen (J. Clinical Invest 73, 889, 1984 and by J Sirois (Adv. Lipid Res. 21, 78, 1985).

The product 12-HETE has been found in high levels in epidermal tissue of patients with psoriasis. The lipoxins have recently been shown to stimulate elastase and superoxide ion release from neutrophils.

Thus, lipoxygenase enzymes are believed to play an important role in the biosynthesis of mediators of asthma, allergy, arthritis, psoriasis, and inflammation. these enzymes interrupts the biochemical pathways believed to be involved in these disease states.

SUMMARY OF THE INVENTION

This invention relates to compounds, compositions and a method for inhibiting lipoxygenase enzymes, in a mammal in need of such treatment by administering to such mammals a composition that comprises a nontoxic pharmaceutically acceptable carrier and a compound of formula I, or its pharmaceutically acceptable cation, in an amount effective to inhibit such activity. A compound of the invention has a structure that corresponds to the general formula below:

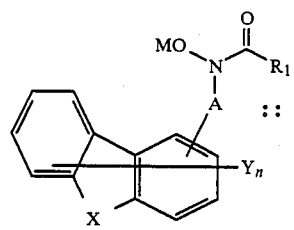

wherein $R_1$ is hydrogen, C1 to C4 alkyl, C2 to C4 alkenyl, or $NR_2R_3$ and $R_2$ and $R_3$ are independently selected from hydrogen, C1 to C4 alkyl or hydroxyl, but $R_2$ and $R_3$ are not simultaneously hydroxyl;

X is oxygen, sulfur, SO2, or $NR_4$ wherein $R_4$ is hydrogen, C1 to C6 alkyl, C1 to C6 alkoyl or aroyl;

A is selected from C1 to C6 alkylene and C2 to C6 alkenylene;

Y is selected independently at each occurrence from hydrogen, halogen, hydroxy, cyano, nitro, halosubstituted alkyl, C1 to C12 alkyl, C2 to C12 alkenyl, C1 to C12 alkoxy, C3 to C8 cycloalkyl, aryl, aryloxy, aroyl, C1 to C12 arylalkyl, C2 to C12 arylalkenyl, C1 to C12 arylalkoxy, C1 to C12 arylthioalkoxy, and substituted derivatives of aryl, aryloxy, aroyl, C1 to C12 arylalkyl, C2 to C12 arylalkenyl, C1 to C12 arylalkoxy, or C1 to C12 arylthioalkoxy, wherein substituents are selected from halo, nitro, cyano, C1 to C12 alkyl, alkoxy, and halosubstituted alkyl; n is a number having values of 0-4; the group(s) Y may be substituted from any of the positions on the aryl rings; when n=0 then Y= hydrogen;

and M is hydrogen, a pharmaceutically acceptable cation, aroyl, or C1 to C12 alkoyl.

A preferred embodiment of the present invention is where X=—NR4. A more preferred embodiment is where X=NR4 and R4 =1-6 alkyl, Y= hydrogen, halogen, alkoxy, alkyl, hydroxy, aryl, nitro, arylalkyl, aroyl and substituted aryl, arylalkyl, arylalkoxy, and aroyl; and n=0-2.

DETAILED DESCRIPTION OF THE INVENTION

In accordance with the present invention, there are 5- and/or 12-lipoxygenase inhibiting compounds of the formula:

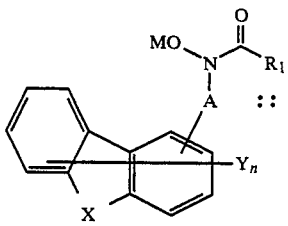

wherein $R_1$ is hydrogen, C1 to C4 alkyl, C2 to C4 alkenyl, or $NR_2R_3$ and $R_2$ and $R_3$ are independently selected from hydrogen, C1 to C4 alkyl or hydroxyl, but $R_2$ and $R_3$ are not simultaneously hydroxyl;

X is oxygen, sulfur, SO2, or $NR_4$ wherein $R_4$ is hydrogen, C1 to C6 alkyl, C1 to C6 alkoyl or aroyl;

A is selected from C1 to C6 alkylene and C2 to C6 alkenylene;

Y is selected independently at each occurrence from hydrogen, halogen, hydroxy, cyano, halosubstituted alkyl, C1 to C12 alkyl, C2 to C12 alkenyl, C1 to C12 alkoxy, C3 to C8 cycloalkyl, aryl, aryloxy, aroyl, C1 to C12 arylalkyl, C2 to C12 arylalkenyl, C1 to C12 arylalkoxy, C1 to C12 arylthioalkoxy, and substituted derivatives of aryl, aryloxy, aroyl, C1 to C12 arylalkyl, C2 to C12 arylalkenyl, C1 to C12 arylalkoxy, or C1 to C12 arylthioalkoxy, wherein substituents are selected from halo, nitro, cyano, C1 to C12 alkyl, alkoxy, and halosubstituted alkyl; n is a number having the values 0–4; the group(s) Y may be substituted from any of the positions on the aryl rings; when n=0 then Y= hydrogen;

and M is hydrogen, a pharmaceutically acceptable cation, aroyl, or C1 to C12 alkoyl.

One embodiment of this invention is compounds of formula I wherein X=O and R1, A, Y and M are as defined above.

A preferred embodiment of this invention is where X=O, Y= hydrogen, halogen, nitro, alkyl, aryl, aroyl, alkoxy, arylalkyl, hydroxy and substituted aryl, arylalkyl or aroyl; and n=0–2.

Examples of compounds which are themselves within the scope of the present invention include the following:

N-hydroxy-N-(1-dibenzofur-3-ylethyl) acetamide
N-hydroxy-N-(1-dibenzofur-3-ylethyl) urea
N-hydroxy-N-(1-dibenzofur-3-ylethyl) N'-methyl urea
N-hydroxy-N-(1-dibenzofur-1-ylethyl) urea
N-hydroxy-N-(1-dibenzofur-2-ylethyl) urea
N-hydroxy-N-(1-dibenzofur-4-ylethyl) urea
N-hydroxy-N-(dibenzofur-3-ylmethyl) N'ethyl urea
N-hydroxy-N-[1-(6-nitrodibenzofur-3-yl)ethyl] N'N'-dimethyl urea
N,N-dihydroxy-N-(1-dibenzofur-3-ylethyl) urea
N-hydroxy-N-(1-dibenzofur-3-ylethyl) formamide
N-hydroxy-N-(1-dibenzofur-3-ylethyl) butanamide
N-hydroxy-[1-(4-chlorodibenzofur-3-yl) ethyl]2-methylpropanamide
N-hydroxy-N-(1-dibenzofur-3-ylethyl) propenamide
N-hydroxy-N-(1-methyl-1-dibenzofur-3-ylethyl) urea
N-hydroxy-N-(2-dibenzofur-3-ylethyl) urea
N-hydroxy-N-[1-methyl-2-(8-methoxy-dibenzofur-3-yl)ethyl] urea
N-hydroxy-N-[3-(6-methoxy-dibenzofur-3-ylpropyl) urea
N-hydroxy-N-(3-dibenzofur-3-ylprop-1-yl) urea
N-hydroxy-N-(1-methyl-3-dibenzofur-3-ylprop-1-yl) urea
N-hydroxy-N-[1-(6-fluoro-dibenzofur-3-yl)ethyl]ura
N-hydroxy-N-[1-(7-phenylmethyl-dibenzofur-3-yl)ethyl] urea
N-hydroxy-N-[1-(5-(4-methylbenzoyl)-dibenzofur-3-yl)ethyl]urea
N-hydroxy-N-[1-(2-hydroxy-dibenzofur-3-yl)ethyl] urea
N-hydroxy-N-(1-dibenzofur-3-ylethyl) urea sodium salt
N-hydroxy-N-(1-dibenzofur-3-ylethyl) acetamide ammonium salt
N-hydroxy-N-(1-dibenzofur-3-ylethyl) urea tetrabutylammonium salt
N-butyloxy-N-(1-dibenzofur-3-ylethyl) urea Another embodiment of this invention is compounds of formula I wherein X=S or SO2.

A preferred embodiment of this invention is where X=S or SO2 and Y= hydrogen, alkyl, aryl, arylalkyl, hydroxy, alkoxy, aroyl, nitro, or substituted aryl, alkyl, arylalkyl or aroyl; and n=0–2.

Examples of compounds which are themselves within the scope of this embodiment include the following:
N-hydroxy-N-(1-dibenzothien-3-ylethyl) urea
N-hydroxy-N-(1-dibenzothien-3-ylethyl) urea 1,1-dioxide
N-hydroxy-N-[1-(6-phenyl-dibenzothien-3-yl)ethyl] urea
N-hydroxy-N-[1-(6-(4-flourophenyl)methoxy-dibenzothien-3yl)ethyl]urea
N-hydroxy-N-(1-dibenzothien-3-ylethyl) urea potassium salt
N-hydroxy-N-[1-dibenzothien-3-yl)ethyl] urea
N-hydroxy-N-[1-(6-phenyl-dibenzothien-3-yl)ethyl] urea
N-hydroxy-N-(dibenzothien-3-ylmethyl) N'-methyl urea
N-hydroxy-N-(dibenzothien-3-ylmethyl) acetamide
N-hydroxy-N-(1-dibenzothien-1-ylethyl) urea
N-hydroxy-N-(1-dibenzothien-2-ylethyl) urea
N-hydroxy-N-(dibenzothien-4-ylethyl) urea
N-hydroxy-N-(dibenzothien-3-ylmethyl) N'ethyl urea
N-hydroxy-N-[1-(6-nitro-1-dibenzothien-3-yl)ethyl]N'N'-dimethyl urea
N-hydroxy-N-(1-dibenzothien-3-ylethyl)formamide
N-hydroxy-N-(1-dibenzothien-3-ylethyl)butamide
N-hydroxy-N-[1-(4-chlorodibenzothien-3-yl)ethyl]-2-methylpropanamide
N,N'-dihydroxy-N-(1-dibenzothien-3-ylethyl) urea
N-hydroxy-N-(1-dibenzothien-3ylethyl) propenamide
N-hydroxy-N-(1-methyl-1-dibenzothien-3-ylethyl) urea
N-hydroxy-N-(2-dibenzothien-3ylethyl) urea
N-hydroxy-N-[2-methyl-2-(8-methoxy-dibenzothien-3-yl)ethyl]urea
N-hydroxy-N-[3-(6-methyl-dibenzothien-3-ylpropyl) urea
N-hydroxy-N-(3-dibenzothien-3-ylprop-1-yl) urea
N-hydroxy-N-[1-methyl-3-(dibenzothien-3-yl)prop-1-yl] urea
N-hydroxy-N-[1-(6-fluoro-dibenzothien-3-yl)ethyl] urea
N-hydroxy-N-[1-(7-phenylmethyl-dibenzothien-3-yl)ethyl] urea
N-hydroxy-N-[1-(6-(4-fluorophenylmethoxy)-dibenzothien-3-yl) ethyl] urea
N-hydroxy-N-[1-(2-hydroxydibenzothien-3-yl)ethyl] urea
N-hydroxy-N-[1-(5,6-dimethyl-dibenzothien-3-yl)ethyl] urea
N-hydroxy-N-(1-dibenzothien-3-ylethyl)urea 1,1-dioxide
N-hydroxy-N-[1-(5-(4-methylbenzoyl)dibenzothien-3-yl)ethyl] urea
N-butyroxy-N-(1-dibenzothien-3-ylethyl) urea
N-hydroxy-N-(1-dibenzothien-3-ylethyl) acetamide ammoniumsalt Another embodiment of this is invention is compounds of formula I wherein X=NR4.

A preferred embodiment of the present invention is where X=—NR4, R4=1-6 alkyl, Y= hydrogen, halogen, alkoxy, alkyl, hydroxy, nitro, aryl, arylalkyl, aroyl and substituted aryl, arylalkyl, arylalkoxy, and aroyl; n=0–2.

Examples of compounds which are themselves within the scope of this particular invention include the following:
N-hydroxy-N-(9-methylcarbaz-3-ylmethyl) N'-ethyl urea
N-hydroxy-N-[1-(6-nitro-9- methylcarbaz-3-yl)ethyl]

N'N'-dimethyl urea
N,N'-dihydroxy-N-[1-(9-methylcarbaz-3-yl)ethyl] urea
N-hydroxy-N-[1-(9-methylcarbaz-3-yl)ethyl]formamide
N-hydroxy-N-[1-(9-methylcarbaz-3-yl)ethyl]butanamide
N-hydroxy-N-[1-(4-chloro-9-methylcarbaz-3-yl)ethyl]2-methylpropanamide
N-hydroxy-N-[1-(9-methylcarbaz-3-yl)ethyl]propenamide
N-hydroxy-N-[1-methyl-1-(9-methylcarbaz-3-yl)ethyl] urea
N-hydroxy-N-[2-(9-methylcarbaz-3-yl)ethyl] urea
N-hydroxy-N-[2-methyl-2-(8-methoxy-9-methylcarbaz-3-yl)ethyl]urea
N-hydroxy-N-[3-(6-methyl-9-methylcarbaz-3-yl)propyl] urea
N-hydroxy-N-[3-(9-methylcarbaz-3-yl)prop-1-yl] urea
N-hydroxy-N-[1-methyl-3-(9-methylcarbaz-3-yl)prop-1-yl] urea
N-hydroxy-N-(1-carbazol-3-ylethyl) urea
N-hydroxy-N-[1-(9-(1-methylethyl)carbazol-3-yl)ethyl] urea
N-hydroxy-N-[1-(9-acetyl-carbazol-3-ylethyl) urea
N-hydroxy-N-[1-(9-benzoyl-carbazol-3-ylethyl) urea
N-hydroxy-N-[1-(6-fluoro-9-methylcarbaz-3-yl)ethyl] urea
N-hydroxy-N-[1-(7-phenylmethyl-9-methylcarbaz-3-yl)ethyl] urea
N-hydroxy-N-[1-(5-(4-methylbenzoyl)-9-methylcarbaz-3-yl)ethyl]urea
N-hydroxy-N-[1-(6-(4-fluorophenylmethoxy)-9-methylcarbaz-3-y 1)ethyl] urea
N-hydroxy-N-[1-(2-hydroxy-9-methylcarbaz-3-yl)ethyl] urea
N-hydroxy-N-[1-(9-ethyl-carbaz-3-ylethyl] urea sodium salt
N-hydroxy-N-[1-(9-ethyl-carbaz-3-ylethyl] urea potassium salt
N-hydroxy-N-[1-(9-ethylcarbaz-3-ylethyl)urea tetrabutylammonium salt The term "alkylene" is used herein to mean straight or branched chain spacer radicals such as —CH2—G, —CHCH3—, —C(CH3)2—, —CH(C2H5)—, —CH2CH2—, —CH2CHCH3—, —C(CH3)2C(CH3)2—, —CH2CH2CH2- and the like.

The term "alkenylene" is used herein to mean straight or branched chain unsaturated spacer radicals such as —CH=CH-, —CH=CHCH2—, CH=CHCH(CH3)—, —C(CH3)=CHCH2—, —CH2CH=CHCH2—, —C(CH3)2CH=CHC(CH3)2—, and the like.

The term "alkyl" is used herein to mean straight or branched chain radicals of 1 to 12 carbon atoms, including, but not limited to methyl, ethyl, n-propyl, isopropyl, n-butyl, sec-butyl, isobutyl, tert-butyl, and the like.

The term "alkenyl" is used herein to mean straight or branched chain unsaturated radicals of 2 to 12 carbon atoms, including, but not limited to ethenyl, 1-propenyl, 2-propenyl, 2-methyl-1-propenyl, 1-butenyl, 2-butenyl, and the like.

The term "cycloalkyl" is used herein to mean cyclic radicals, preferably of 3 to 8 carbons, including, but not limited to cyclopropyl, cyclobutyl, cyclopentyl, cyclohexyl, and the like. The term "alkoxy" is used herein to mean —OR5 wherein R5 is an alkyl radical, including, but not limited to methoxy, ethoxy, isopropoxy, n-butoxy, sec-butoxy, isobutoxy, tert-butoxy, and the like.

The term "alkoyl" is used herein to mean —COR6 wherein R6 is an alkyl radical, including, but not limited to formyl, acetyl, propionyl, butyryl, isobutyryl, pivaloyl, and the like. The term "carboalkoxy" is used herein to mean —COR7 wherein R7 is an alkoxy radical, including, but not limited to carbomethoxy, carboethoxy, carboisopropoxy, carbobutoxy, carbosec-butoxy, carboiso- butoxy, carbotert-butoxy, and the like. The term "aryl" is used herein to mean substituted and unsubstituted aromatic radicals wherein the substituents are chosen from halo, nitro, cyano, C1 to C12 alkyl, alkoxy, and halo substituted alkyl, including, but not limited to phenyl, 1- or 2-naphthyl, and the like.

The term "aroyl" is used herein to mean —COR8 wherein R8 is an aryl radical, including, but not limited to benzoyl, 1-naphthoyl, 2-naphthoyl, and the like.

The term "aryloxy" is used herein to mean —OR9 wherein R9 is an aryl radical, including, but not limited to phenoxy, 1-naphthoxy, 2-naphthoxy and the like.

The term "arylalkoxy" is used herein to mean -OR10 wherein R10 is an arylalkyl radical, including, but not limited to phenylmethoxy (i.e., benzyloxy), 4-fluorobenzyloxy, 1-phenylethoxy, 2-phenylethoxy, diphenylmethoxy, 1-naphthylmethyloxy, 2-napthylmethyloxy, 9-fluorenoxy, 2—, 3- or 4-pyridylmethoxy, 2-, 3-, 4-, 5-, 6-, 7-, 8-quinolylmethoxy and the like.

The term "arylthioalkoxy" is used herein to mean —SR11 wherein R11 is an arylalkyl radical, including, but not limited to phenylthiomethoxy (i.e., thiobenzyloxy), 4-fluorothiobenzyloxy, 1-phenylthioethoxy, 2-phenylthioethoxy, diphenylthiomethoxy, 1-naphthylthiomethoxy and the like.

The term "arylalkyl" is used herein to mean an aryl group appended to an alkyl radical, including, but not limited to phenylmethyl(benzyl), 1-phenylethyl, 2-phenylethyl, 1-naphthylethyl and the like.

The term "arylalkenyl" is used herein to mean an aryl group appended to an alkenyl radical, including, but not limited to phenylethenyl, 3-phenylprop-1-enyl, 3-phenylprop-2-enyl, 1-naphthylethenyl and the like.

The terms "halo" and "halogen" are used herein to mean radicals derived from the elements fluorine, chlorine, bromine, and iodine.

The term "halosubstituted alkyl" refers to an alkyl radical as described above substituted with one or more halogens, including, but not limited to chloromethyl, trifluoromethyl, 2,2,2-trichloroethyl, and the like.

The term "pharmaceutically acceptable cation" refers to non-toxic cations including but not limited to cations based on the alkali and alkaline earth metals, such as sodium, lithium, potassium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

The term "lipoxygenase" is used herein to mean 5- and/or 12-lipoxygenase.

The compounds of the invention inhibit lipoxygenase, which makes the compounds useful in the treatment and prevention of disease states wherein lipoxygenase may be involved, including, but not limited to, asthma, rheumatoid arthritis, gout, psoriasis, allergic rhinitis, adult respiratory distress syndrome, Crohn's disease, endotoxin shock, benign prostatic hypertrophy, inflammatory bowel disease and/or ischemia induced myocardial or brain injury.

FORMULATION OF PHARMACEUTICAL COMPOSITIONS

This invention provides for compositions in unit dosage form for the inhibition of 5- or 12-lipoxygenase activity in a human or lower animal host in need of such treatment, comprising a compound of this invention and one or more nontoxic pharmaceutically acceptable carriers, adjuvants or vehicles which are collectively referred to herein as carriers. The amount of active ingredient that may be combined with such materials to produce a single dosage form will vary depending upon various factors, as indicated above.

A variety of materials can be used as carriers, adjuvants and vehicles in the composition of this invention, as available in the pharmaceutical arts. Injectable preparations, such as oleaginous solutions, suspensions or emulsions, may be formulated according to known art, using suitable dispersing or wetting agents and suspending agents, as needed. The sterile injectable preparation may employ a nontoxic parenterally acceptable diluent or solvent as, for example, sterile nonpyrogenic water or 1,3 -butanediol.

Among the other acceptable vehicles and solvents that may be employed are 5% dextrose injection, Ringer's injection and isotonic sodium chloride injection (as described in the USP/NF). In addition, sterile, fixed oils are conventionally employed as solvents or suspending media. For this purpose any bland fixed oil may be used, including synthetic mono-, di- or triglycerides. Fatty acids such as oleic acid can also be used in the preparation of injectable compositions.

Suppositories for rectal administration of the compound of this invention can be prepared by mixing the drug with suitable nonirritating excipient such as cocoa butter and polyethylene glycols, which are solid at ordinary temperatures but liquid at body temperature and which therefore melt in the rectum and release the drug.

Solid dosage forms for oral administration include capsules, tablets, pills, troches, lozenges, powders and granules. In such solid dosage forms, the active compound may be admixed with at least one inert diluent such as sucrose, lactose or starch. Such dosage forms may also comprise, as is normal practice, pharmaceutical adjuvant substances, e.g., stearate lubricating agents. In the case of capsules, tablets and pills, the dosage forms may also comprise buffering agents. Solid oral preparations can also be prepared with enteric or other coatings which modulate release of the active ingredients.

Liquid dosage forms for oral administration include pharmaceutically acceptable emulsions, solutions, suspensions, syrups and elixirs containing inert nontoxic diluents commonly used in the art, such as water and alcohol. Such compositions may also comprise adjuvants, such as wetting agents, emulsifying suspending, sweetening, flavoring and perfuming agents.

METHOD OF TREATMENT

This invention provides a method of inhibiting 5- and/or 12-lipoxygenase activity in a human or lower animal host in need of such treatment which method comprises administration to the human or lower animal host a compound of the previously described composition of Formula I in an amount effective to inhibit lipoxygenase activity in the host. This invention also provides a method of treating asthma, rheumatoid arthritis, gout, psoriasis, allergic rhinitis, adult respiratory distress syndrome, Crohn's disease, endotoxin shock, and/or ischemia-induced myocardial injury in a human or lower animal in need of such treatment comprising administering to the human or lower animal a therapeutically effective amount of a compound of the previously described composition. Further, this invention provides a method for treatment and prevention of symptoms of the disease states mentioned above.

The compounds of the present invention may be administered orally, parenterally or topically in dosage unit formulations containing conventional nontoxic pharmaceutically acceptable carriers, adjuvants and vehicles as desired.

The term parenteral as used herein includes subcutaneous, intravenous, intraarterial injection or infusion techniques, without limitation. The term "topically" encompasses administration rectally and by inhalation spray, as well as by the more common routes of the skin and the mucous membranes of the mouth and nose.

Total daily dose of the compounds of this invention administered to a host in single or divided doses may be in amounts, for example, of from about 0.001 to about 100 mg/kg body weight daily and more usually 0.01 to 10 mg/kg/day. Dosage unit compositions may contain such amounts of such submultiples thereof as may be used to make up the daily dose. It will be understood, however, that the specific dose level for any particular patient will depend upon a variety of factors including the body weight, general health, sex, diet, time and route of administration, rates of absorption and excretion, combination with other drugs and the severity of the particular disease being treated.

SYNTHESIS OF THE COMPOUNDS

Compounds of this invention can be prepared according to the reaction sequence described in Scheme 1. The compounds in each of the following examples are abreviated using the terms of R1, A, X and Y and A as defined before. The position on the tricylic rings for substituents A and Y are listed as numerals which correspond to their position on the tricyclic rings and is based upon IUPAC nomenclature or as found in the Handbook of Chemistry and Physics, CRC Press, 54th Edition, 1973. In addition, if the A and Y substituents are written with a hypen to the left of the group this indicates a bond to their position on the tricyclic ring. For instance A=3—CH(CH3)—describes a methylene linkage to the 3-position on the tricyclic ring, and to the ntrogen group, and has additional substitution, in this case, of a methyl group.

Although the reaction sequence illustrates a compound of formula I wherein R1 is methyl, A is —CH(CH3)—, X is oxygen or NCH2CH3 and Y is hydrogen, it will be seen from the examples that other compounds of this invention can be prepared in the same manner using the appropriate starting materials. All temperature ranges noted are in degrees centigrade unless indicated otherwise.

Scheme 1

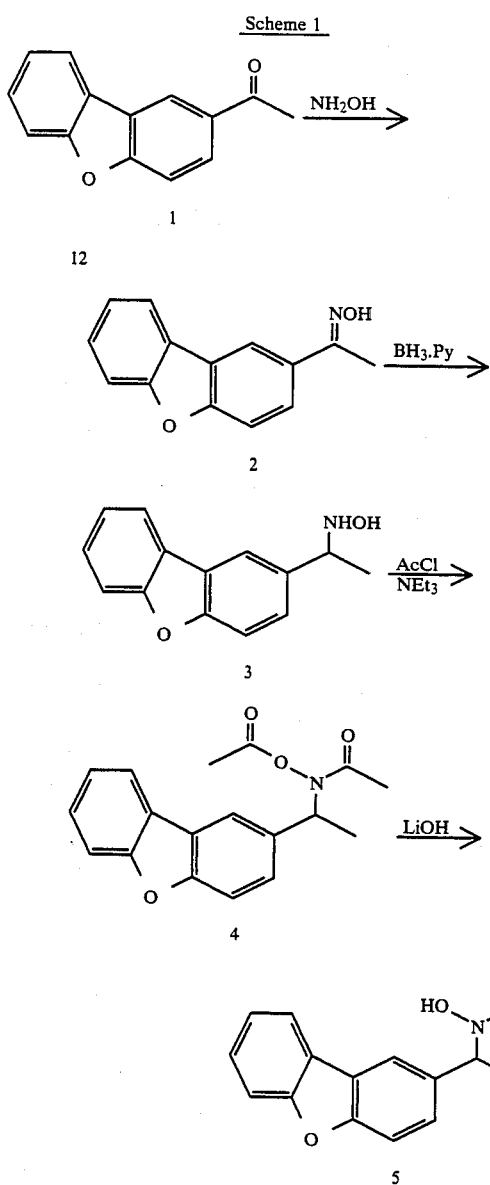

3-Acetyldibenzo[b]furan 1 is treated with hydroxyl amine in ethanol/pyridine to produce the oxime 2. This is reduced to the hydroxylamine 3 with borane pyridine complex and then converted to the N,O-diacetate 4 with acetyl chloride and triethylamine. The diacetate is converted to the hydroxamic acid 5 by hydrolysis with lithium hydroxide. 9-Ethyl-3-acetylcarbazole may be substituted for the compound of FIG. 1 thereby thereby producing the final compounds of FIG. 5 wherein X=NR4.

Other reagents may also be used to carry out the same transformation. For example 2 may be converted to 3 using borane dimethyl amine, borane-tetrahydrofuran, or other borane complexes. Intermediate 2 may also be converted to 3 with sodium cyanoborohydride or with phenyldimethylsilane in trifluoroacetic acid. Hydroxylamine 3 can also be converted to 4 with acylating agents such as acetic anhydride in the presence of other bases such as pyridine.

Compounds of formula I wherein R1 is NR4R5 can be prepared according to the method outlined in scheme 2, below. Although the sequence illustrates the case where R1 is NH2, A is —CH(CH3)—, X is oxygen and Y is hydrogen, it will be seen from the following examples that other compounds of this invention can also be prepared in this manner.

Scheme 2

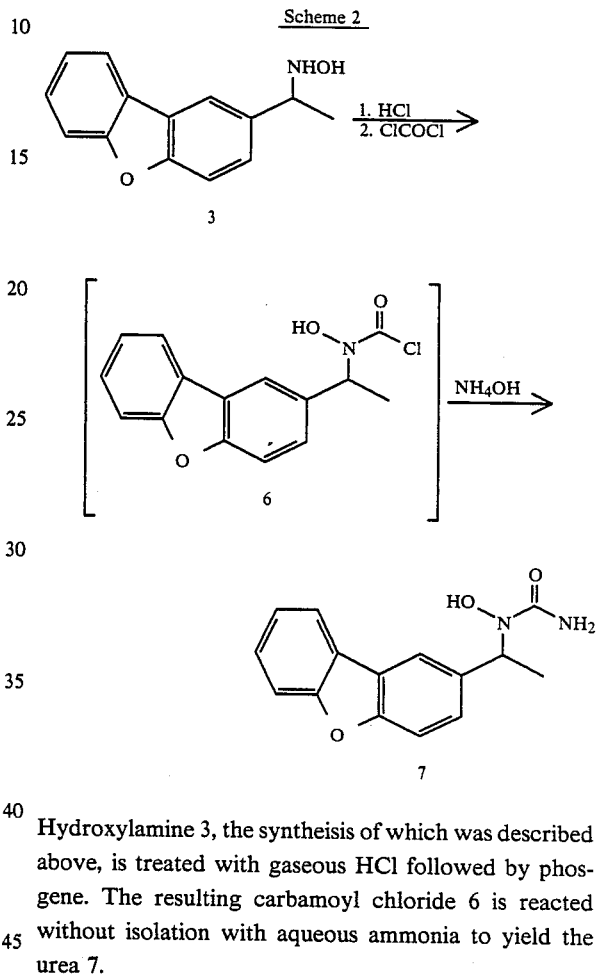

Hydroxylamine 3, the syntheisis of which was described above, is treated with gaseous HCl followed by phosgene. The resulting carbamoyl chloride 6 is reacted without isolation with aqueous ammonia to yield the urea 7.

Compounds of formula I, where R1 is NR4R5 and where at least one of either R4 or R5 is hydrogen can also be prepared according to Scheme 3, below. The sequence illustrates the case where R1 is NH2(i.e.,R4 and R5 are both hydrogen), A is —CH(CH3)—, X is oxygen and Y is hydrogen. However, other compounds of this invention such as X=NCH2CH3 or NR4 can also be prepared in this manner.

Scheme 3

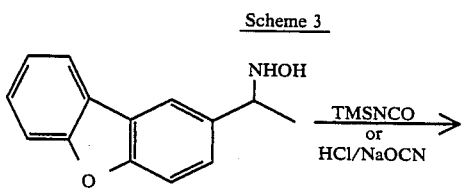

-continued
Scheme 3

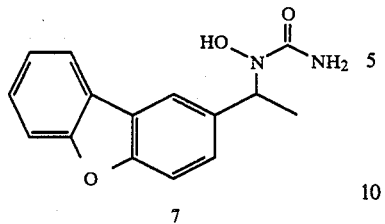
7

Hydroxylamine 3 is treated with trimethylsilyl isocyanate (TMSNCO), followed by ammonium chloride workup to give the urea 7. Alternatively, 3 can be treated with sodium cyanate in an acidic solution to yield the urea 7.

In addition to the methods described above, hydroxylamines such as 3 can be prepared as shown in scheme 4, below. The scheme illustrates the case where R1 is methyl, A is —CH(CH3)—, X is oxygen, and Y is hydrogen. However other compounds of this invention can also be prepared in this manner.

Scheme 4

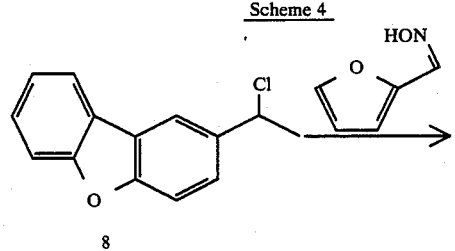
8

-continued
Scheme 4

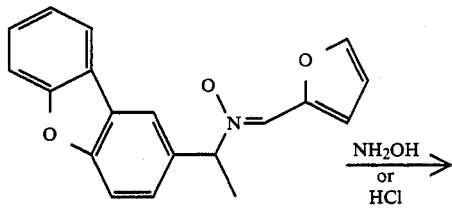
9

Chloride 8 is treated with Z-furfuraldehyde oxime and a base such as sodium methoxide to give nitrone 9. The nitrone is then hydrolyzed under acidic conditions or with hydroxylamine. The hydroxylamine can be converted to compounds such as 5 and 7 using the methodology described above. Compounds with other leaving groups such as bromides, iodides, tosylates, mesylates, triflates can be used instead of chloride 8.

In addition to the methods described above compounds of this invention may also be prepared as described in scheme 5, below. The scheme illustrates the case where R1 is methyl, A is —CH(CH3)—, X is oxygen, and Y is hydrogen. However other compounds of this invention can also be prepared as described in scheme 5, below. The scheme illustrates the case where R1 is methyl, A is —CH(CH3)—, X is oxygen, and Y is hydrogen. However other compounds of this invention can also be prepared in this manner.

Scheme 5

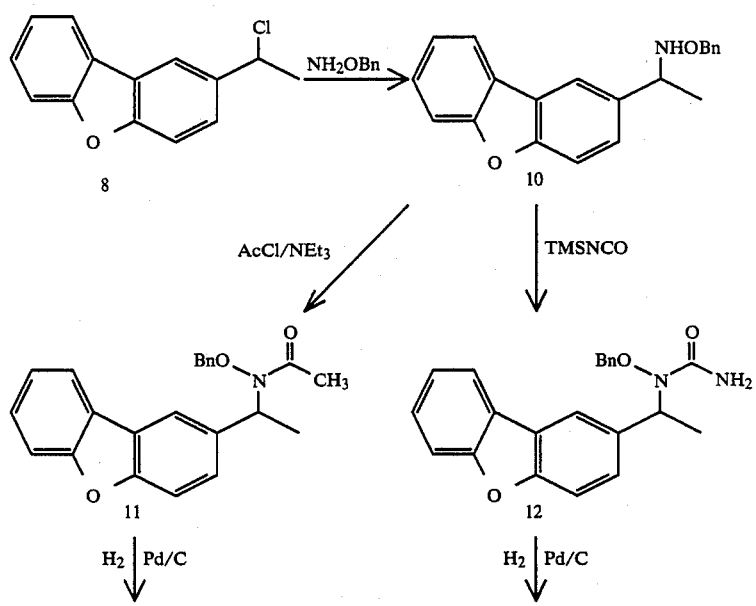

Scheme 5

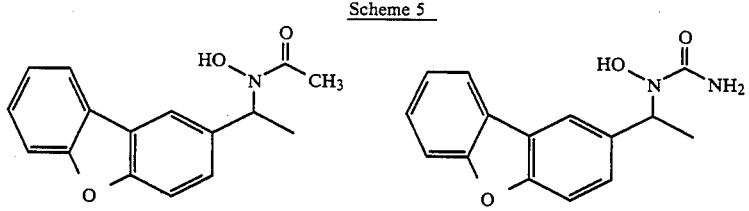

-continued

Chloride 8 is heated with O-benzylhydroxylamine in a solvent such as dimethylsulfoxide or tetrahydrofuran to yield the new hydroxylamine 10. This can either be reacted with acetyl chloride as in scheme 1 to yield 11 or with trimethylsilyl isocyanate as in scheme 3 to yield 12. Compounds 11 and 12 are then hydrogenated to yield 5 and 7 respectively. Other O-protected hydroxylamines may also be used in place of O-benzylhydroxylamine such as O-tetrahydropyranyl hydroxylamine. Further other methods may be used to convert 10 to 7, such as treatment with phosgene followed by ammonium hydroxide such as described in scheme 2, or treatment with sodium cyanate as described in scheme 3.

Compounds of this invention in which A is —CH2— or —CH(alkyl)— may also be prepared as described in scheme 6. This scheme illustrates the synthesis of intermediate hydroxylamine 10 but other compounds of this invention can also be prepared using this method.

Scheme 6

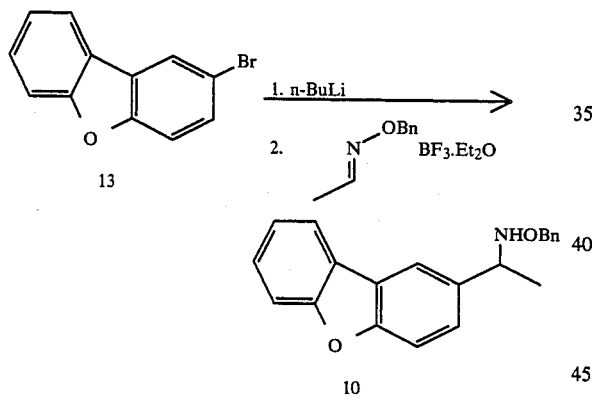

Bromide 13 is converted to 3-lithio dibenzofuran by treatment with n-butyllithium. This is then treated with the -benzyloxime of acetaldehyde in the presence of BF3.Et2O to give 0-benzylhydroxylamine 10. This may be converted to the compounds such as 5 or 7 as described in scheme 4. Other O-protected oximes may be substituted for the O-benzyl oxime and other Lewis acids such as CeCl3 may be used. The following examples further illustrate the synthesis and use of compounds o f this invention. The appropriate designations for R1, A, X, and Y as defined by formula I are given for each example below.

EXAMPLE 1

N-hydroxy-N-(1-dibenzofur-3-ylethyl) acetamide a. 3-Acetyldibenzofuran. To a magnetically stirred solution of aluminum chloride (40 g, 300 mmole) in nitroethane (220 mL) under dry nitrogen was added acetyl chloride (9.5 g, 120 mmole) at 0°–5°. The solution was stirred for 15 min, then dibenzofuran (16.8 g, 100 mmole) was added slowly and the reaction turned deep yellow-green. After 45 min at 0°, the yellow-green suspension was added to a mixture of ice and 3N HCl. The mixture was extracted with ether (2×300 mL) and extracts were dried (Na2SO4), filtered and concentrated. The crude ketone, a light amber oil, was judged to be sufficiently pure by thin layer chromatography (TLC) to use directly in the next step.

b. 3-Acetyldibenzofuran oxime. The crude ketone prepared as described in step a, was dissolved in pyridine (50 mL) and ethanol (50 mL) and hydroxylamine hydrochloride was added. The mixture was stirred overnight at ambient temperature. The reaction was concentrated and the residue was partitioned between ethyl acetate (300 mL) and 3N HCl. The ethyl acetate layer was dried (Na2SO4), filtered and concentrated in vacuo to give a crystalline residue. The crystals were rinsed with hexane, filtered and dried to give 12.3 g of the desired product, mp 132°–135°.

c. 1-(3-Dibenzofuranyl)ethyl hydroxylamine. Borane-pyridine complex (12.3 g, 133 mmole) was added to a suspension of the crude oxime (10 g, 44 mmole), prepared as in step b, in ethanol (50 mL). Thirty minutes later 6 N HCl (30 mL) was added slowly. After being stirred overnight the reaction was concentrated in vacuo and ice was added followed by 4 N NaOH. The gummy precipitate was extracted with ethyl acetate (2×150 mL) and the extracts were combined, dried over Na2SO4 and concentrated to give crude hydroxyl amine. This was carried on without further purification.

d. N-acetoxy-N-(1-dibenzofur-3-ylethyl) acetamide. Acetic anhydride (9.0 mL) was added to a solution of the crude hydroxylamine, prepared as in step c, and triethyl amine (12.4 mL) in methylene chloride (50 mL). The reaction was stirred overnight, then washed with cold water and 3 N HCl. The methylene chloride layer was dried (Na2SO4) and concentrated to give a yellowish oil. This residue was chromatographed on 100 g of silica gel, eluting with 20% ethyl acetate in hexanes to give the desired product.

e. N-hydroxy-N-(1-dibenzofur-3-ylethyl) acetamide. Lithium hydroxide mono hydrate (0.910 g, 21.7 mmole) in water (15 mL) was added to a solution of the material prepared as described in step d, (3.39 g, 10.9 mmole) in ethanol. After stirring for 30 minutes the solution was concentrated in vacuo. The residue was carefully acidified with 6N HCl, then extracted with ethyl acetate (3×200 mL). The extracts were dried (Na2SO4) filtered and concentrated. The residue was triturated with ether and filtered to give 2.03g of the desired material as white crystals. (R1=CH3, A=3—CH(CH3)—, X=O, Y=H)

Melting Point: 125°5-127°.

NMR (300 MHz, DMSO-d6): 1.54, 1.56 (d, 3H, J=7.0); 2.03, 2.04 (s, 3H); 5.81 (m, 1H); 7.41 (m, 1H); 7.51 (m, 2H); 7.65 (d, 1H, J=8.5); 7.70 (d, 1H, J=8.5); 8.10 (m, 1H); 8.18 (m, 1, J=7.7); 9.60, 9.66 (s, 1H).

Mass spectrum (CI-NH3): 270 (M+1)+, 287 (M+NH4)+, 195.

Analysis (C16H15NO3): Calculated—C: 71.36, H: 5.61, N: 5.20; Found C: 71.05, H: 5.56, N: 5.02.

EXAMPLE 2

N-hydroxy-N-(1-dibenzofur-3-ylethyl) urea

Trimethylsilyl isocyanate (1.2 mL) was added to a solution of 1-(3-dibenzofuranyl)ethyl hydroxylamine (0.88 g, 3.87 mmole), prepared as described in Example 1, step c, in THF (6 mL). The mixture was heated at 60° for one hour and then poured into saturated NH4Cl solution. This was extracted with ethyl acetate (3×100 mL). The organic layer was concentrated in vacuo and the residue was triturated with ether to give the desired product as a white solid (0.84 g, 80%). (R1=NH2, A=—CH(CH3)—, X=O, Y=H)

Melting Point: 171°–173°.

NMR (300 MHz, DMSO-d6): 1.52 (d, 3H, J=7.0); 5.48 (q, 1 H, J=7.0); 6.34 (s, 2H); 7.39 (dt, 1H, J=0.9, J=7.5); 7.51 (m, 2H); 7.62 (d, 1 H, J=8.6); 7.69 (d, 1 H, J=8.2); 8.10 (d, 1H, J=1.5), 8.14 (m, 1H, J=7.3); 9.11 (s, 1H).

Mass spectrum (CI-NH3): 271 (M+1)+, 288 (M+NH4)+, 195.

Analysis (C15H14N2O3): Calculated—C: 66.65, H: 5.22, N: 10.37; Found C: 66.49, H: 5.10, N: 10.29.

EXAMPLE 3

N-hydroxy-N-(1-dibenzofur-3-ylethyl) N'-methyl urea

The desired material was prepared as described in Example 2, except using methyl isocyanate instead of trimethylisocyanate. (R1=NHCH3, A=3—CH(CH3)—, X=O, Y=H)

Melting Point: 157°–159°.

NMR (300 MHz, DMSO-d6): 1.51 (d, 3H, J=7.4); 2.58 (d, 3H, J=4.4); 3.35 (s, 3H); 6.87 (q, 1H, 4.4); 7.39 (td, 1H, J=7.4, J=1.1); 7.51 (m, 2H); 7.62 (d, 1H, J=8.4); 7.68 (d, 1H, J=8.4); 7.68 (d, 1H, J=8.1); 8.10 (d, 1H, J=1.5); 8.15 (m, 1 H); 9.02 (s, 1H).

Mass spectrum (CI-NH3): 302 (M+1)+, 285 (M+NH4)+, 195.

Analysis (C16H16N2O3): Calculated—C: 67.59, H: 5.67, N: 9.86; Found C: 67.21, H: 5.65, N: 9.80.

EXAMPLE 4

N-hydroxy-N-(9-ethylcarbaz-3-ylmethyl) N-methyl urea a. 9-Ethyl-3-formylcarbazole oxime. 9-Ethyl-3-carbazole carboxaldehyde (5 g, 22.4 mmole) was dissolved in pyridine (50 mL) and ethanol (50 mL) and hydroxylamine hydrochloride (2.3 g, 33.6 mmole) was added. The mixture was stirred overnight at ambient temperature. The reaction was concentrated and the residue was partitioned between ethyl acetate (300 mL) and 3N HCl. The ethyl acetate layer was dried (MgSO4), filtered and concentrated in vacuo to give a crystalline residue. The crystals were rinsed with hexane, filtered and dried to give 5.7 g of the desired product.

b. 9-Ethylcarbazo-3-ylmethyl hydroxylamine. Borane-pyridine complex (5.34 g, 57.5 mmole) was added to a suspension of the crude oxime (5.7 g, 23 mmole), prepared as in step a, in ethanol (150 mL). Thirty minutes later 6 N HCl (30 mL) was added slowly. After being stirred overnight the reaction was concentrated in vacuo and ice was added followed by 4 N NaOH. The gummy precipitate was extracted with ethyl acetate (2×150 mL) and the extracts were combined, dried over Na2SO4 and concentrated to give crude hydroxyl amine. This was carried on without further purification.

c. N-hydroxy-N-(1-9-ethylcarbazo-3-ylmethyl) N-methyl urea. Methyl isocyanate (0.86 g, 15 mmole) was added to a solution of the crude hydroxylamine (2.4g, 10.0 mmole), prepared as in step b in THF (15 mL). The solution was stirred for 30 minutes at room temperature and then the solvent was removed in vacuo. The residue was recrystallized from ethyl acetate to give a white solid (1.7g). (R1=NHCH3, A=3—CH2-, X=NC2H5, Y=H)

Melting Point: 170°–172°.

NMR (300 MHz, DMSO-d6): 1.28 (t, 3H, 7.5); 2.62 (d, 3H, J=5.5); 4.42 (q, 2H, J=2.5); 4.65 (s, 2H); 6.68 (q, 1H, J=5.5); 7.17 (m, 1H); 7.41 (m, 2H), 7.55 (m, 2H); 8.02 (m, 1H); 8.10 (m, 1H); 9.24 (s, 1H).

Mass spectrum (CI-NH3): 298 (M+1)+, 315 (M+NH4)+, 208.

Analysis (C17H19N3O2): Calculated—C: 68.67, H: 6.44, N: 14.31; Found C; 68.54, H: 6.34, N: 14.11.

EXAMPLE 5

N-hydroxy-N-[1-(9-ethylcarbaz-3-yl)ethyl] urea

The desired material was prepared according to the method of example 4, except using 9-ethyl-3-acetylcarbazole instead of 9-ethyl-3-formylcarbazole. (R1=NH2, A=3—CH(CH3)—, X=NC2H5, Y=H)

Melting Point: 139°–142° (dec).

NMR (300 MHz, DMSO-d6): 1.30 (t, 3H, J=7.5); 1.53 (d, 3H); J=7.5); 4.41 (q, 2H, J=7.5); 5.49 (q, 1H, J=7.5); 6.27 (brs, 2H); 7.18 (m, 1H); 7.35–7.62 (m, 4H); 8.02–8.16 (m, 2H); 9.04 (brs, 1H).

Mass spectrum (CI-NH3): 298 (M+1)+, 315 (M+NH4)+, 222.

EXAMPLE 6

N-hydroxy-N-(9-ethylcarbaz-3-ylmethyl) acetamide a. N-acetoxy-N-(1-(9-ethylcarbaz-3-ylmethyl) acetamide. Acetic anhydride is added to a solution of 9-ethylcarbazo-3-yl-methyl hydroxylamine, prepared as in example 4, in step b, and triethyl amine in methylene chloride. The reaction is stirred overnight, then washed with cold water and 3 N HCl. The methylene chloride layer is dried (Na2SO4) and concentrated to give the desired material.

b. N-hydroxy-N-(9-ethylcarbaz-3-ylmethyl) acetamide. Lithium hydroxide mono hydrate in water is added to a solution of the material prepared as described in step a in ethanol. After stirring for 30 minutes the solution was concentrated in vacuo. The residue is carefully acidified with 6N HCl, then extracted with ethyl acetate. The extracts are dried (Na2SO4) filtered and concentrated to give the desired material. (R1=CH3, A=-3—CH2—, X=NC2H5, Y=H). The compounds of Examples 7–57 may be prepared in a manner generally analogous to Examples 1-6, and/or schemes 1-6.

EXAMPLE 7

9N-hydroxy-N-(dibenzothien-3-ylmethyl) N'-methyl urea (R1=NHCH3, A=3—CH2—, X=S, Y=H)

EXAMPLE 8

N-hydroxy-N-[1-(dibenzothien-3-yl)ethyl] urea (R1=NH2, A=3—CHCH3—, X=S, Y=H)

EXAMPLE 9
N-hydroxy-N-(dibenzothien-3-ylmethyl) acetamide (RI=CH3, A=3—CH2—, X=S, Y=H)

EXAMPLE 10
N-hydroxy-N-(1-dibenzothien-1-ylethyl) urea (R1=NH2, A=1—CHCH3—, X=S, Y=H)

EXAMPLE 11
N-hydroxy-N-(1-dibenzothien-2-ylethyl) urea (R1=NH2, A=2—CHCH3—, X=S, Y=H)

EXAMPLE 12
N-hydroxy-N-(dibenzothien-4-ylethyl) urea (R1=NH2, A=4—CHCH3—, X=S, Y=H)

EXAMPLE 13
N-hydroxy-N-[1-(9-methylcarbaz-2-yl)ethyl] urea ((R1=NH2, A=2—CH(CH3)—, X=NCH3, Y=H)

EXAMPLE 14
N-hydroxy-N-[1-(9-methylcarbaz-4-yl)ethyl] urea (R1=NH2, A=4—CH(CH3)—, X=NCH3, Y=H)

EXAMPLE 15
N-hydroxy-N-(dibenzothien-3-ylmethyl) N-ethyl urea (R1=NHC2H5, A=3—CH2—, X=S, Y=H)

EXAMPLE 16
N-hydroxy-N-[1-(6-nitro-1-dibenzothien-3-yl)ethyl]N,N'-dimethyl urea (R1=N(CH3)2, A=3—CH(CH3)—, X=S, Y=6-NO2)

EXAMPLE 17
N,N'-dihydroxy-N-(1-dibenzothien-3-ylethyl) urea (R1=NHOH, A=3—CH(CH3)—, X=S, Y=H)

EXAMPLE 18
N-hydroxy-N-(9-methylcarbaz-3-ylmethyl) N'-ethyl urea (R1=NHC2H5, A=3—CH2—, X=NCH3, Y=H)

EXAMPLE 19
N-hydroxy-N-[1-(6-nitro-9-methylcarbaz-3-yl)ethyl]N'N'-dimethyl urea (R1=N(CH3)2, A=3—CH(CH3)—, X=NCH3, Y=6-NO2)

EXAMPLE 20
N,N'-dihydroxy-N-[1-(9-methylcarbaz-3-yl)ethyl] urea (R1=NHOH, A=3—CH(CH3)—, X=NCH3, Y=H)

EXAMPLE 21
N-hydroxy-N-(1-dibenzothien-3-ylethyl) formamide (R1=H, A=3—CH(CH3)—, X=S, Y=H)

EXAMPLE 22
N-hydroxy-N-(1-dibenzothien-3-ylethyl) butanamide (R1=C3H7, A=3—CH(CH3)—, X=S, Y=H)

EXAMPLE 23
N-hydroxy-N-[I-(4-chlorodibenzothien-3 -yl)ethyl]2-methylpropanamide (R1=CH(CH3)2, A=3—CH(CH3)—, X=S, Y=4—Cl)

EXAMPLE 24
N-hydroxy-N-[1-(9-methylcarbaz-3-yl)ethyl]formamide (R1=H, A=3—CH(CH3)—, X=NCH3, Y=H)

EXAMPLE 25
N-hydroxy-N-[1-(9-methylcarbaz-3-yl)ethyl]butanamide (R1=C3H7, A=3—CH(CH3)—, X=NCH3, Y=H)

EXAMPLE 26
N-hydroxy-N-[1-(4-chloro-9-methylcarbaz-3-yl)ethyl]2-methylpropanamide (R1=CH(CH3)2, A=3—CH(CH3)—, X=NCH3, Y=4—Cl)

EXAMPLE 27
N-hydroxy-N-(1-dibenzothien-3-ylethyl) propenamide (R1=CH=CH2, A=3—CH(CH3)—, X=S, Y=H)

EXAMPLE 28
N-hydroxy-N-(1-methyl-1-dibenzothien-3-ylethyl) urea (R1=NH2, A=3—C(CH3)2—, X=S, Y=H)

EXAMPLE 29
N-hydroxy-N-(2-dibenzothien-3-ylethyl) urea (R1=NH2, A=3—CH2CH2—, X=S, Y=H)

EXAMPLE 30
N-hydroxy-N-[I-(9-methylcarbaz-3-yl)ethyl]propenamide (R1 =CH=CH2, A=3—CH(CH3)—, X=NCH3, Y=H)

EXAMPLE 31
N-hydroxy-N-[1-methyl-1-(9-methylcarbaz-3-yl)ethyl] urea (R1=NH2, A=3—C(CH3)2—, X=NCH3, Y=H)

EXAMPLE 32
N-hydroxy-N-[2-(9-methylcarbaz-3-yl)ethyl] urea (R1=NH2, A=3—CH2CH2—, X=NCH3, Y=H)

EXAMPLE 33
N-hydroxy-N-[2-methyl-2-(8-methoxy-dibenzothien-3-yl)ethyl]urea (R1=NH2, A=3—CH2CH(CH3)—, X=S, Y=8—CH3O)

EXAMPLE 34
N-hydroxy-N-[3-(6-methyl-dibenzothien-3-ylpropyl) urea (R1=NH2, A=3—CH2CH2CH2—, X=S, Y=6—CH3)

EXAMPLE 35

N-hydroxy-N-(3-dibenzothien-3-ylprop-1-yl) urea (R1=NH2, A =3—CH=CHCH2—, X=S, Y=H)

EXAMPLE 36

N-hydroxy-N-[2-methyl-2-(8-methoxy-9-methylcarbaz-3-yl)ethyl]urea (R1=NH2, A=3—CH2CHCH3—, X=NCH3, Y=-8—CH3O)

EXAMPLE 37

N-hydroxy-N-[3-(6-methyl-9-methylcarbaz-3-yl)propyl] urea (R1=NH2, A=3—CH2CH2CH2—, X=NCH3, Y=6—CH3)

EXAMPLE 38

N-hydroxy-N-[3-(9-methylcarbaz-3-yl)prop-1-yl] urea (R1=NH2, A=3—CH=CHCH2—, X=NCH3, Y=H)

EXAMPLE 39

N-hydroxy-N-(1-methyl-3-(dibenzothien-3-yl)prop-1-yl) urea (R1=NH2, A=3—C(CH3)=CHCH2—, X=S, Y=H)

EXAMPLE 40

N-hydroxy-N-[1-methyl-3-(9-methylcarbaz-3-yl)prop-1-yl] urea (R1=NH2, A=3—C(CH3)=CHCH2—, X=NCH3, Y=H)

EXAMPLE 41

N-hydroxy-N-(1-carbazol-3-ylethyl) urea (R1=NH2, A=3—CH(CH3)—, X=NH, Y=H)

EXAMPLE 42

N-hydroxy-N-[1-(9-(1-methylethyl)carbazol-3-yl)ethyl] urea (R1=NH2, A=3—CH(CH3)—, X=N(CH(CH3)2), Y=H)

EXAMPLE 43

N-hydroxy-N-[1-(9-acetyl-carbazol-3-ylethyl) urea (R1=NH2, A=3—CH(CH3)—, X=NCOCH3, Y=H)

EXAMPLE 44

N-hydroxy-N-[1-(9-benzoyl-carbazol-3-ylethyl) urea (R1=NH2, A=3—CH(CH3)—, X=NCOC6H5, Y=H)

EXAMPLE 45

N-hydroxy-N-(1-dibenzothien-3-ylethyl) urea 1,1-dioxide (R1=CH3, A=3—CH(CH3)—, X=SO2, Y=H)

EXAMPLE 46

N-hydroxy-N-[1-(6-phenyl-dibenzothien-3-yl)ethyl] urea (R1=NH2, A=3—CH(CH3)—, X=S, Y=-6—C6H5)

EXAMPLE 47

N-hydroxy-N-[1-(6-fluoro-dibenzothien-3-yl)ethyl] urea (R1=NH2, A=3—CH(CH3)—, X=S, Y=6-F)

EXAMPLE 48

N-hydroxy-N-[1-(7-phenylmethyl-dibenzothien-3-yl)ethyl] urea (R1=NH2, A=3—CH(CH3)—, X=S, Y=-7—C6H5CH2)

EXAMPLE 49

N-hydroxy-N-[1-(5-(4-methylbenzoyl)-dibenzothien-3-yl)ethyl]urea (R1=NH2, A=3—CH(CH3)—, X=S, Y=5-(4—CH3C6H4)CO)

EXAMPLE 50

N-hydroxy-N-[1-(6-fluoro-9-methylcarbaz-3-yl)ethyl] urea (R1=NH2, A=3—CH[CH3)—, X=NCH3, Y=6-F)

EXAMPLE 51

N-hydroxy-N-[1-(7-phenylmethyl-9-methylcarbaz-3-yl)ethyl] urea (R1=NH2, A=3—CH(CH3)—, X=NCH3, Y=-7—C6H5CH2)

EXAMPLE 52

N-hydroxy-N-[1-(5-(4-methylbenzoyl)-9-methylcarbaz-3-yl)ethyl]urea (R1=NH2, A=3—CH(CH3)—, X=NCH3, Y=5-(4—CH3C6H4)CO)

EXAMPLE 53

N-hydroxy-N-[1-(6-(4-fluorophenylmethoxy)-dibenzothien-3-yl) ethyl] urea (R1=NH2, A=3—CH(CH3)—, X=S, Y=6-(4-FC6H4)CH2O)

EXAMPLE 54

N-hydroxy-N-[1-(2-hydroxydibenzothien-3-yl)ethyl] urea (R1=NH2, A=3—CH(CH3)—, X=S, Y=2-OH)

EXAMPLE 55

N-hydroxy-N-[1-(6-(4-fluorophenylmethoxy)-9-methylcarbaz-3-yl)-ethyl] urea (R1=NH2, A=3—CH(CH3)—, X=NCH3, Y=6-(4-FC6H4)CH2O)

EXAMPLE 56

N-hydroxy-N-[1-(2-hydroxy-9-methylcarbaz-3-yl)ethyl] urea (R1=NH2, A=3—CH(CH3)—, X=NCH3, Y=2-OH)

EXAMPLE 57

N-hydroxy-N-[1-(5,6-dimethyl-dibenzothien-3-yl)ethyl] urea (R1=NH2, A=3—CH(CH3)—( X=S, Y=5,6-(CH3)2)

EXAMPLE 58

N-hydroxy-N-[1-(9-ethyl-carbaz-3-ylethyl] urea sodium salt

The material prepared as in Example 5 may be dissolved in tetrahydrofuran and one equivalent of sodium hydride added. After hydrogen evolution ceases, hexane may be added and the desired product collected by filtration. (R1=NH2, A=3—CH(CH3)—, X=NCH2CH3, Y=H, M=Na)

EXAMPLE 59

N-hydroxy-N-[1-(9-ethyl-carbaz-3-ylethyl] urea potassium salt

The material prepared as in Example 5 may be dissolved in tetrahydrofuran and one equivalent of potassium hydride added. After hydrogen evolution ceases, hexane may be added and the desired product collected by filtration. (R1=NH2, A=3—CH(CH3)—, X=NCH2CH3, Y=H, M=K)

EXAMPLE 60

N-hydroxy-N-(1-dibenzothien-3-ylethyl) acetamide ammoniumsalt

The material prepared as in Example 8 may be dissolved in tetrahydrofuran and ammonia bubbled through the solution. Hexane may be added and the desired product collected by filtration. (R1=CH3, A=3—CH(CH3]-, X=S, Y=H, M=NH4)

EXAMPLE 61

N- hydroxy-N-[1-(9-ethylcarbaz-3-ylethyl) urea tetrabutylammonium salt

The material prepared as in Example 7 may be dissolved in tetrahydrofuran and one equivalent of tetrabutyl ammonium hydroxide added. Hexane may be added and the desired product collected by filtration. (R1=NH2, A=3—CH(CH3)-, X=NCH2CH3, Y=H, M=N(C4H9)4)

EXAMPLE 62

N-butyroxy-N-(1-dibenzothien-3-ylethyl) urea

The material prepared as in Example 10 and 1.1 equivalents of triethylamine may be dissolved in tetrahydrofuran and 1 equivalent of butyryl chloride added. Ether may be added and the material washed with 2N HCl, dried with MgSO4 and evaporated to yield the desired product. (R1=NH2, A=3—CH(CH3)—, X=S, Y=H, M=COC3H7)

The compounds of Examples 63–82 may be prepared in a manner generally analogous to examples 1 and 2, or schemes I-6.

EXAMPLE 63

N-hydroxy-N-(1-dibenzofur-1-ylethyl) urea (R1=NH2, A=1—CH(CH3)—, X=O, Y=H)

EXAMPLE 64

N-hydroxy-N-(1-dibenzofur-2-ylethyl) urea (R1=NH2, A=2—CH(CH3)—, X=O, Y=H)

EXAMPLE 65

N-hydroxy-N-(1-dibenzofur-4-ylethyl) urea (R1=NH2, A=4—CHCH3—, X=O, Y=H)

EXAMPLE 66

N-hydroxy-N-(dibenzofur-3-ylmethyl) N'-ethyl urea (R1=NHC2H5, A=3—CH2—, X=O, Y=H)

EXAMPLE 67 urea

N-hydroxy-N-[1-(6-nitrodibenzofur-3-yl)ethyl]N'N'-dimethyl urea (R1=N(CH3)2, A=3—CH(CH3)—, X=O, Y=6-NO2)

EXAMPLE 68

N,N'-dihydroxy-N-(1-dibenzofur-3-ylethyl) urea (R1=NHOH, A=3—CH(CH3)—, X=O, Y=H)

EXAMPLE 69

N-hydroxy-N-(1-dibenzofur-3-ylethyl) formamide (R1=H, A=3—CH(CH3)—, X=O, Y=H)

EXAMPLE 70

N-hydroxy-N-(1-dibenzofur-3-ylethyl) butanamide (R1=C3H7, A=3—CH(CH3)—, X=O, Y=H)

EXAMPLE 71

N-hydroxy-N -[1 -(4-chlorodibenzofur-3 -yl) ethyl]2-methylpropanamide (R1=CH(CH3)2, A=3—CH(CH3)—, X=O, Y=-4—Cl)

EXAMPLE 72

N-hydroxy-N-(1-dibenzofur-3-ylethyl) propenamide (R1=CH=CH2, A=3—CH(CH3)—, X=O, Y=H)

EXAMPLE 73

N-hydroxy-N-(1-methyl-1-dibenzofur-3-ylethyl) urea (R1=NH2, A=3—C(CH3)2—, X=O, Y=H)

EXAMPLE 74

N-hydroxy-N-(2-dibenzofur-3-ylethyl) urea (R1=NH2, A=3—CH2CH2—, X=0, Y=H)

EXAMPLE 75

N-hydroxy-N-[1-methyl-2-(8-methoxy-dibenzofur-3-yl)ethyl] urea (R1=NH2, A=3—CH2CH(CH3)—, X=O, Y=-8—CH3O)

EXAMPLE 76

N-hydroxy-N-[3-(6-methyl-dibenzofur-3-ylpropyl) urea (R1=NH2, A=3—CH2CH2CH2—, X=O, Y=-6—CH3)

EXAMPLE 77

N-hydroxy-N-(3-dibenzofur-3-ylprop-1-yl) urea (R1=NH2, A=3—CH=CHCH2—, X=O, Y=H)

EXAMPLE 78

N-hydroxy-N-(1-methyl-3-dibenzofur-3-ylprop-1-yl) urea (R1=NH2, A=3—C(CH3)=CHCH2—, X=O, Y=H)

EXAMPLE 79

N-hydroxy-N-[1-(6-fluoro-dibenzofur-3-yl)ethyl] urea (R1=NH2, A=3—CH(CH3)—, X=O, Y=6-F)

EXAMPLE 80

N-hydroxy-N-[1-(7-phenylmethyl-dibenzofur-3-yl)ethyl] urea (R1=NH2, A=3—CH(CH3)—, X=O, Y=-7—C6H5CH2)

EXAMPLE 81

N-hydroxy-N-[1-(5-(4-methylbenzoyl)—dibenzofur-3-yl)ethyl]urea (R1=NH2, A=3—CH(CH3)—, X=O, Y=5-(4—CH3C6H4)CO)

EXAMPLE 82

N-hydroxy-N-[1-(2-hydroxy-dibenzofur-3-yl)ethyl] urea (R1=NH2, A=3—CH(CH3)—, X=O, Y=2-OH)

EXAMPLE 83

N-hydroxy-N-(1-dibenzofur-3-ylethyl) urea sodium salt

The material prepared as in Example 2 may be dissolved in tetrahydrofuran and one equivalent of sodium hydride added. After hydrogen evolution ceases, hexane may be added and the desired product collected by filtration. (R1=NH2, A=3—CH(CH3)—, X=O, Y=H, M=Na)

EXAMPLE 84

N-hydroxy-N-(1-dibenzothien-3-ylethyl) urea potassium salt

The material prepared as in Example 8 may be dissolved in tetrahydrofuran and one equivalent of potassium hydride added. After hydrogen evolution ceases, hexane may be added and the desired product collected by filtration. (R1=NH2, A=3—CH(CH3)—, X=S, Y=H, M=K)

EXAMPLE 85

N-hydroxy-N-(1-dibenzofur-3-ylethyl) acetamide ammonium salt

The material prepared as in Example 2 may be dissolved in tetrahydrofuran and ammonia bubbled through the solution. Hexane may be added and the desired product collected by filtration. (R1=CH3, A=3-CHCH3—, X=O, Y=H, M=NH4)

EXAMPLE 86

N-hydroxy-N-(1-dibenzofur-3-ylethyl) urea tetrabutylammonium salt

The material prepared as in Example 2 may be dissolved in tetrahydrofuran and one equivalent of tetrabutyl ammonium hydroxide added. Hexane may be added and the desired product collected by filtration. (R1=NH2, A=3—CHCH3—, X=O, Y=H, M=N(C4H9)4)

EXAMPLE 87

N-butyroxy-N-(I-dibenzofur-3-ylethyl) urea

The material prepared as in Example 2 and 1.1 equivalents of triethylamine may be dissolved in tetrahydrofuran and 1 equivalent of butyryl chloride added. Ether may be added and the material is washed with 2N HCl, dried with MgSO4 and evaporated to yield the desired product. (R1=NH2, A=3—CH(CH3)—, X=O, Y=H, M=COC3H7)

EXAMPLE 88

Lipoxygenase IC50 Determination

Assays to determine 5-lipoxygenase activity were performed in 200 mL incubations containing the 20,000xg supernatant from $6 \times 10^4$ homogenized RBL-1 cells, 2% DMSO vehicle and various concentrations of the test compound. Reactions were initiated by addition of radiolabelled arachidonic acid and terminated by acidification and ether extraction. Reaction products were separated from nonconverted substrate by thin layer chromatography and measured by liquid scintillation spectroscopy. All treatments were evaluated in triplicate incubations. Inhibition of 5-lipoxygenase activity was computed by comparison of the quantity of products formed in the treatment incubations to the mean product formation in vehicle control groups (n=8). IC50 values and 95% confidence limits were computed by linear regression analysis of percentage inhibition versus log inhibitor concentration plots. The results of the assay indicate that the compounds are inhibitors of 5-lipoxygenase.

TABLE 1

In vitro 5-lipoxygenase inhibitory potency of compounds of this invention.

| Example | R1 | A | X | Y | IC50($\mu$M) |
|---|---|---|---|---|---|
| 1 | CH3 | CHCH3 | O | H | 0.29 |
| 2 | NH2 | CHCH3 | O | H | 0.23 |
| 3 | NHCH3 | CHCH3 | O | H | 0.29 |
| 4 | NH2 | CH2 | NC2H5 | H | 0.39 |
| 5 | NH2 | CHCH3 | NC2H5 | H | 0.38 |

The forgoing is merely illustrative of the invention and is not intended to limit the invention to the disclosed compounds. Variations and changes which are obvious to one skilled in the art are intended to be within the scope and nature of the invention which are defined in the appended claims.

What is claimed is:

1. A compound of the formula:

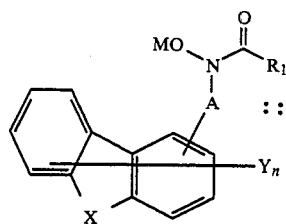

wherein
R1 is hydrogen, C1 to C4 alkyl, C2 to C4 alkenyl, or NR2R3, wherein R2 and R3 are independently selected from hydrogen, C1 to C4 alkyl and hydroxyl, but R2 and R3 are not simultaneously hydroxyl;

X is NR4, wherein R4 is hydrogen, C1 to C6 alkyl, C1 to C6 alkoyl or aroyl;

A is selected from C1 to C6 alkylene and C2 to C6 alkenylene;

Y is selected independently at each occurrence from hydrogen, halogen, hydroxy, cyano, nitro, halosubsititued alkyl, C1 to C12 alkyl, C2 to C12 alkenyl, C1 to C12 alkenul, C1 to C12 alkoxy, c3 to c8 cycloalkyl aroyl, C1 to C12 arylalkyl, C2 to C12 arylalkenyl, C1 to C12 arylalkoxy, C1 to C12 arylthioalkoxy, and substituted derivatives of aryl-,aryloxy, aroyl, C1 to C12 arylalkyl, C2 to C12 arylalkenyl, C1 to C13 arylalkoxy, or C1 to C12 arylthioalkoxy, wherein substituents are selected from halo, nitro, cyano, C1 to C13 alkyl, alkoxy, and halosubstituted alkyl; n is a number having the values of 0–4; when n=0 then Y=hydrogen;

and M is hydrogen, a pharmaceutically acceptable cation, aroyl, or C1 to C12 alkoyl.

2. A compound according to claim 1 wherein Y=alkyl, aryl, hydrogen, arylalkyl, hydroxy,, alkoxy, aroyl, or substituted aryl, alkyl, arylalkyl or aroyl; and n=0–2.

3. A compound according to claim 1 where R4=1–6 alkyl, Y=hydrogen, halogen, alkoxy, alky, hydroxy, aryl, arylalkyl, aroyl and substituted aryl, arylalkyl, arylalkoxy, and arcyl; and n=0–2.

4. A compound according to claim 1 wherein R1 is Nr2R3, wherein R2 and R3 are independently selected from hydrogen, C1 to C4 alkyl and hydroxyl, but R2 and R3 are not simultaneously hydroxyl.

5. A compound according to claim 1 wherein R1 is hydrogen, C1 to C4 alkyl, or C2 to C4 alkenyl.

6. A pharmaceutical composition for inhibitiong 5- and/or 12-lipoxygenase, comprising a pharmaceutical carrier and a therapeutically effective amount of a compound of claim 1.

7. A method for inhibiting 5-and/or 12-lipoxygenase activity comprising administering to a human or lower animal in need of such treatment, a therapeutically effective amount of a compound of the formula:

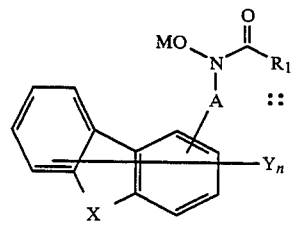

wherein
R1 is hydrogen, C1 to C4 alkyl, C2 to C4 alkenyl, or NR2R3, wherein R2 and R3 are independently selected from hydrogen, C1 to C4 alkyl and hydroxyl, but R2 and R3 are not simultaneously hydroxyl, X is NR4, wherein R4 is hydrogen, C1 to C6 alkyl, C1 to C6 alkylene and C2 to C6 alkenylene;

Y is selected independently at each occurrence from hydrogen, halogen hydroxy, cyano, nitro, halosubstituted alkyl, C1 to C12 alkyl, C2 to C12 alkenyl, C1 to C12 alkoxy, C3 to C8 cycloalkyl, aryl, aryloxy, aroyl, C1 to C12 arylalkyl, C2 to C12 arylalkenyl, C1 to C12 arylalkoxy, C1 to C12 arylthioalkoxy, and substituted derivatives of aryl, aryloxy, aroyl, C1 to C12 arylalkyl, C2 to C12 arylalkenyl, C1 to C12 arylalkoxy, or 1 to C13 arylthioalkoxy, wherein substituents are selected from halo, nitro, cyano, C1 to C12 alkyl, alkoxy, and haloslubstituted alkyl; n is a number having the values 0–4; when n=0 then Y= hydrogen;

and M is hydrogen, a pharmaceutically acceptable cation, aroyl, or C1 to C12 alkoyl.

8. The method of claim 7 wherein R1 is hydrogen, C1 to C4 alkyl, or C2 to C4 alkenyl.

9. The method of claim 7 wherein R1 is NR2R3, wherein R2 and R3 are independently selected from hydrogen, C1 to C4 alkyl and hydroxyl, but R2 and R3 are not simultaneously hydroxyl.

10. The method of claim 7 wherein A is —CHCH3—.

UNITED STATES PATENT AND TRADEMARK OFFICE
CERTIFICATE OF CORRECTION

PATENT NO. : 4,822,811
DATED : April 18, 1989
INVENTOR(S) : James B. Summers

It is certified that error appears in the above-identified patent and that said Letters Patent is hereby corrected as shown below: ON TITLE PAGE:

In the Abstract, Column 2: replace the structure with the following:

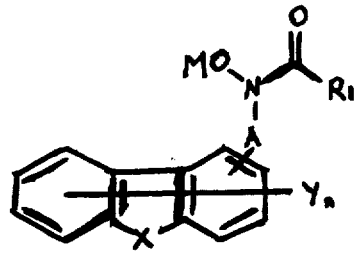

In the Abstract, Column 2: in the definition of X, replace "$CO_2$ with --$SO_2$--.

Column 1, line 56: before "these" insert --Blocking--.

Column 2, line 5: replace the structure with the following:

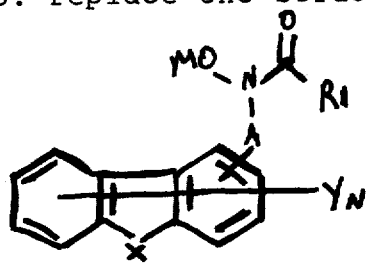

Column 2, line 55: replace the structure with the following:

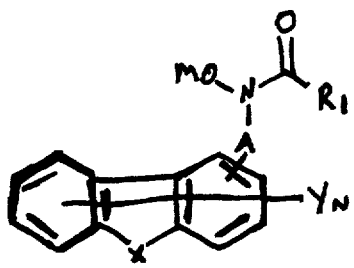

UNITED STATES PATENT AND TRADEMARK OFFICE
CERTIFICATE OF CORRECTION

PATENT NO. : 4,822,811
DATED : April 18, 1989
INVENTOR(S) : James B. Summers

It is certified that error appears in the above-identified patent and that said Letters Patent is hereby corrected as shown below:

Column 3, line 50: Replace "ethyl]ura" with --ethyl] urea--.

Column 4, line 9: Replace "thien-3 yl)" with --thien-3-yl)--.

Column 4, line 55: Replace "moniumsalt" with --monium salt--.

Column 5, line 43: Replace "-CH$_2$-G should read --CH$_2$--.

Column 12, Scheme 4: Replace the structure with the following:

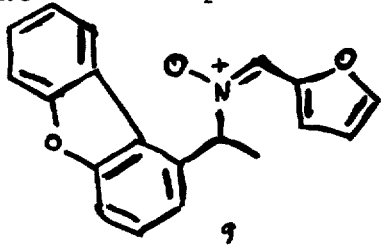

Column 12, line 35: After prepared delete "as described in scheme 5, below. The scheme illustrates the case where R1 is methyl, A is --CH(CH3)--, X is oxygen, and Y is hydrogen. However other compounds of this invention can also be prepared"

Column 13, line 50: Replace "benzyloxime" with --O-benzyloxime--.

Column 14, line 64, Replace "125°5-127°" with --125°-127°--.

Column 19, line 43: Replace X⁺NH, Y⁺H)" with --X=NH,  Y=H)--.

UNITED STATES PATENT AND TRADEMARK OFFICE
CERTIFICATE OF CORRECTION

PATENT NO. : 4,822,811

DATED : April 18, 1989

INVENTOR(S) : James B. Summers

It is certified that error appears in the above-identified patent and that said Letters Patent is hereby corrected as shown below:

Column 21, line 12: Replace "A=3-CH(CH3)-(" with --A=3-CH(CH3)-,--.

Column 25, line 5: replace the structure with the following:

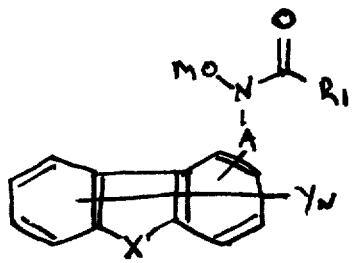

Column 25, line 26: Delete "C1 to C12 alkenul".

Column 25, line 26: Replace "c3 to c8" with --C3 to C8--.

Column 25, line 27: After "cycloalkyl" and before "aroyl" insert --, aryl, aryloxy,--.

Column 25, line 29: Replace "aryl-" with --aryl,--.

Column 25, line 30: Replace ",aryloxy," with --aryloxy--.

Column 25, line 31: Replace "C13" with --C12--.

Column 25, line 33: Replace "C13" with --C12--.

Column 25, line 41: Replace "R4=1-6" with --R4= C1-C6--.

UNITED STATES PATENT AND TRADEMARK OFFICE
CERTIFICATE OF CORRECTION

PATENT NO. : 4,822,811
DATED : April 18, 1989
INVENTOR(S) : James B. Summers

It is certified that error appears in the above-identified patent and that said Letters Patent is hereby corrected as shown below:

Column 25, line 36: Replace "acceptableca-" with --acceptable ca- --.

Column 25, line 39: Replace "hydroxy,," with --hydroxy,--.

Column 25, line 42: Replace "alky" with --alkyl--.

Column 25, line 44: Replace "arcyl" with --aroyl--.

Column 25, line 46: Replace "Nr2R3" with --NR2R3--.

Column 26, line 1: Replace "inhibitiong" with --inhibiting--.

Column 26, line 15: Replace the structure with the following:

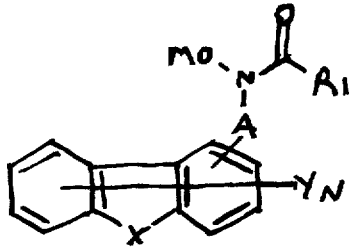

Column 26, Line 25: Replace "droxyl," with --droxyl;--.

UNITED STATES PATENT AND TRADEMARK OFFICE
CERTIFICATE OF CORRECTION

PATENT NO. : 4,822,811
DATED : April 18, 1989
INVENTOR(S) : James B. Summers

It is certified that error appears in the above-identified patent and that said Letters Patent is hereby corrected as shown below:

Column 26, line 26 & 27: Replace "a lkyl, C1 to C6 alkylene and C2 to C6 alkenylene;" with --alkyl, C1 to C6 alkoyl or aroyl;
A is selected from C1 to C6 alkylene and C2 to C6 alkenylene--.

Column 26, line 36: Replace "or 1" with --or Cl--.

Column 26, line 37: Replace "C13" with --C12--.

Column 26, line 39: Replace "haloslubstituted" with --halosubstituted--.

Signed and Sealed this

Seventeenth Day of December, 1991

Attest:

HARRY F. MANBECK, JR.

*Attesting Officer*

*Commissioner of Patents and Trademarks*